(12) United States Patent
Muschol

(10) Patent No.: US 8,854,621 B1
(45) Date of Patent: Oct. 7, 2014

(54) SYSTEMS AND METHODS FOR DETERMINING NANOPARTICLE DIMENSIONS

(71) Applicant: Martin Matthias Muschol, Tampa, FL (US)

(72) Inventor: Martin Matthias Muschol, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/011,055

(22) Filed: Aug. 27, 2013

Related U.S. Application Data

(60) Provisional application No. 61/694,362, filed on Aug. 29, 2012.

(51) Int. Cl.
*G01N 15/02* (2006.01)
*G01N 21/47* (2006.01)
*G01N 21/21* (2006.01)

(52) U.S. Cl.
CPC ............ *G01N 15/0211* (2013.01); *G01N 21/21* (2013.01); *G01N 21/47* (2013.01)
USPC ......................................................... 356/336

(58) Field of Classification Search
CPC ....... B82Y 5/00; B82Y 35/00; G01N 21/6408
See application file for complete search history.

(56) References Cited

U.S. PATENT DOCUMENTS

| | | | | |
|---|---|---|---|---|
| 5,434,667 | A * | 7/1995 | Hutchins et al. | 356/338 |
| 2002/0140425 | A1 * | 10/2002 | Prammer et al. | 324/303 |
| 2008/0218766 | A1 * | 9/2008 | Novotny et al. | 356/496 |
| 2009/0323061 | A1 * | 12/2009 | Novotny et al. | 977/773 |
| 2010/0177311 | A1 * | 7/2010 | Wada | 356/336 |
| 2012/0044493 | A1 | 2/2012 | Smart et al. | |

OTHER PUBLICATIONS

Glidden et al., "Characterizing Gold Nanorods in Solution Using Depolarized Dynamic Light Scattering", Mar. 12, 2013, The Journal of Physical Chemistry, pp. 8128-8137.*

Chapter 6—Advanced Scattering Techniques, Ralf Rohlsberger: Nuclear Condensed Matter Physics with Synchroton Radiation, 2004, pp. 233-271.*

Tirado, M. M., Martinez, C. L., & de la Torre, J. G. (1984). Comparison of theories for the translational and rotational diffusion coefficients of rod-like macromolecules. Application to short DNA fragments. The Journal of chemical physics, 81, 2047.

Ortega, A., & de la Torre, J. G. (2003). Hydrodynamic properties of rodlike and disklike particles in dilute solution. The Journal of chemical physics, 119, 9914.

Glidden, M., & Muschol, M. (2012). Characterizing gold nanorods in solution using depolarized dynamic light scattering. The Journal of Physical Chemistry C, 116(14), 8128-8137.

* cited by examiner

*Primary Examiner* — Tarifur Chowdhury
*Assistant Examiner* — Juan D Valentin, II
(74) *Attorney, Agent, or Firm* — Thomas | Horstemeyer, LLP

(57) ABSTRACT

In one embodiment, the dimensions of nanoparticles are determined by focusing light on a sample of nanoparticles suspended in a solution, collecting light scattered by the nanoparticles, measuring translational and rotational decay rates of the collected light, calculating a ratio of the rotational decay rate to translational decay rate, and estimating a first dimension of the nanoparticles based upon the decay rate ratio.

20 Claims, 7 Drawing Sheets

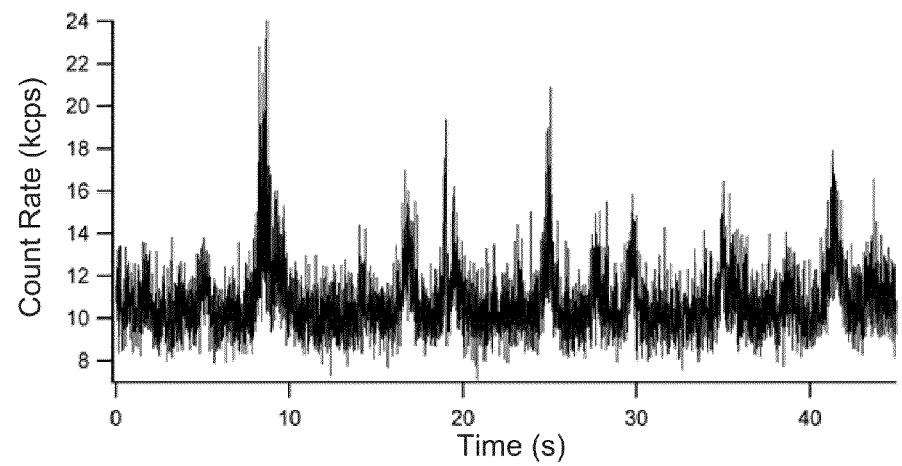
FIG. 3A
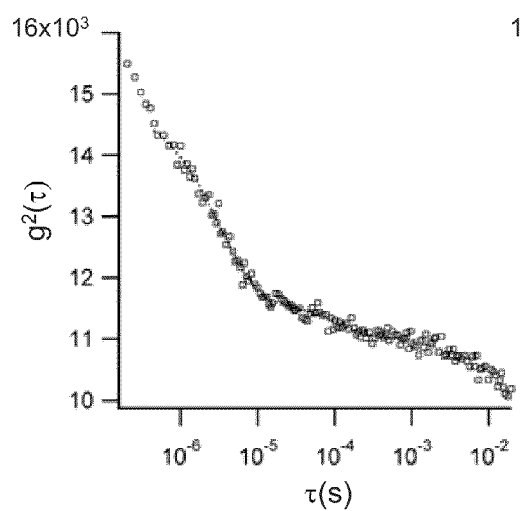 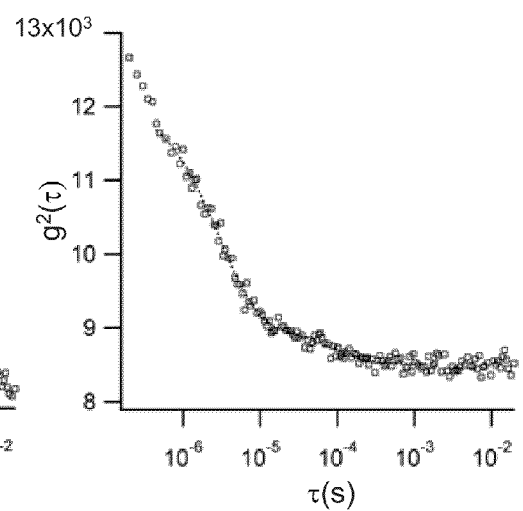
FIG. 3B    FIG. 3C

SYSTEMS AND METHODS FOR DETERMINING NANOPARTICLE DIMENSIONS

CROSS-REFERENCE TO RELATED APPLICATION(S)

This application claims priority to U.S. Provisional Application Ser. No. 61/694,362, filed Aug. 29, 2012, which is hereby incorporated by reference herein in its entirety.

BACKGROUND

Many metallic and semiconducting materials develop intriguing optical, electrical, and magnetic properties at the nanoscale, making them prime targets for the development of nanomaterials with novel functionalities. Such materials are often used to form nanorods. Among the potential applications of nanorods are novel surface coatings including superhydrophobic coatings and electrical and magnetic nanowires and their use as optical metamaterials for long-distance imaging with near-field resolution.

Selecting the length or aspect ratio of metallic nanorods provides a particularly straightforward method for modulating their prominent optical absorption bands. Their near infrared absorption peaks are particularly favorable for biomedical applications. The observation that anisotropic nanorods are more readily taken up into cells than their spherical counterparts has provided additional impetus for development of biomedical applications.

The reliable characterization of the physical and optical properties of nanorods, ideally in their natural solution environment, is critical for evaluating their performance in virtually all of the above-mentioned applications. Currently, the optical absorption spectrum of metallic nanorods and, in particular, the peak wavelength of the longitudinal surface plasmon resonance (LSPR), is used to derive aspect ratios for gold nanorods. However, the relationship between theoretically-predicted and experimentally-observed absorption spectra for metallic nanorods remains controversial. Counter to long-held assumptions, recent theoretical and experimental efforts indicate that the absorption peak of the surface plasmon resonance is not uniquely determined by the geometrical aspect ratio (length/diameter) of the nanorods. In addition, the optical absorption spectrum does not provide a direct measure of the heterogeneity of sizes and shapes often encountered in practice. Although electron microscopy provides an unbiased measure of particle morphologies and size distributions, it does not yield information about growth kinetics. In addition, it does not indicate whether surfactants, commonly used during synthesis or for maintaining solubility of nanoparticles, adsorb onto nanorod surfaces or whether nanorods remain dispersed or begin to interact and/or aggregate in suspension.

From the above discussion it can be appreciated that it would be desirable to have an alternative system and method for determining the dimensions of nanoparticles.

BRIEF DESCRIPTION OF THE DRAWINGS

The present disclosure may be better understood with reference to the following figures. Matching reference numerals designate corresponding parts throughout the figures, which are not necessarily drawn to scale.

FIG. 3A is a graph that plots photon count history for an Au nanorod solution.

FIG. 3B is a graph of a correlation function for the photon count in FIG. 3A calculated prior to removing bursts from the raw photon count.

FIG. 3C is a graph of a correlation function for the photon count in FIG. 3A calculated after removing bursts from the raw photon count.

DETAILED DESCRIPTION

As described above, it would be desirable to have an alternative system and method for determining the dimensions of nanoparticles. Described herein is a custom-designed, depolarized dynamic light scattering system and method for determining nanorod translational and rotational diffusion in situ. In some embodiments, diffusion measurements, in the form of decay rates, obtained by the system are used to directly predict nanorod lengths and aspect ratios.

In the following disclosure, various embodiments are described. It is to be understood that those embodiments are example implementations of the disclosed inventions and that alternative embodiments are possible. All such embodiments are intended to fall within the scope of this disclosure.

Described in the following disclosure is a custom-designed, light scattering system using a time-tagged time-resolved (TTTR) photon collection and processing scheme, as well as a novel approach towards analyzing translational and rotational diffusivities. As described below, this approach was experimentally applied to determine the length and aspect ratios of commercial samples of gold nanorods. It was determined that the length of the nanorod samples can be extracted to within 10-20% of their bare dimensions seen in electron micrographs.

Optical Design of the DDLS System

Figure 1:
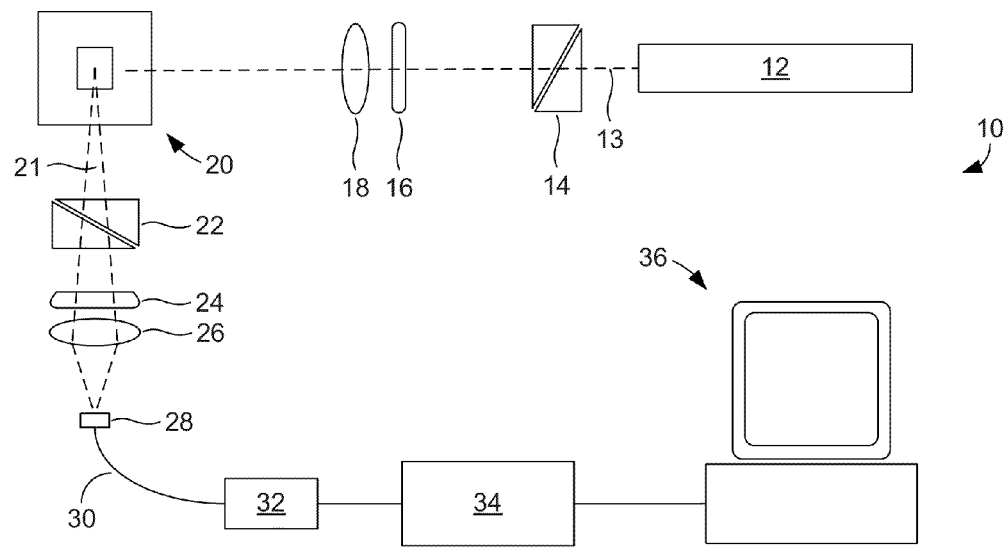
FIG. 1 is a block diagram of an embodiment of a dynamic light scattering system that can be used to determine nanoparticle dimensions.

FIG. 1 illustrates an example depolarized dynamic light scattering (DDLS) system 10 that can be used to determine nanoparticle dimensions. As described below, a system similar to the system 10 shown in FIG. 1 was used to conduct experiments to test the system's ability to accurately determine the dimensions of gold nanorods.

As shown in FIG. 1, the system 10 incorporates an optical design using a 90° scattering geometry. A laser 12 generates a beam of light 13 that passes through a prism 14 that increases the polarization purity to a nominal ratio, such as 100,000:1. By way of example, the laser 12 can be a 35 mW single-mode HeNe laser at $\lambda$=633 nm (e.g., JDS Uniphase, model 1145P) and the prism 14 can be a Glan-Thompson prism.

The polarized beam is focused on a sample chamber 20 using a focusing lens 18. The sample can comprise a plurality of nanoparticles, such as nanorods, that are suspended in a liquid such as water, acetone, tetrahydrofuran (THF), or any appropriate solvent. By way of example, the lens 18 has a focal length of approximately 100 mm, in which case the beam has a beam waist of approximately 80 μm in diameter at the center of the sample holder. In some embodiments, the sample holder can be a sample cuvette that is supported by a cuvette holder having a Peltier temperature controller (e.g., TLC-50, Quantum Northwest). As shown in FIG. 1, an aperture 16 can be used to prevent stray light from entering the lens 18.

Scattered light 21 is collected at 90° relative to the incoming laser beam. A second prism 22, such as a further Glan-Thompson prism, can be used to select either vertically-polarized (v-v) or horizontally-depolarized (v-h) scattered light. An adjustable iris diaphragm 24 can be used to select the solid angle of the scattered light 21 imaged onto a photon detector 32, thereby determining the number of coherence areas that are contributing to the signal. A further focusing lens 26 can be used to focus the scattered light 21 onto the input 28 of an optical fiber 30 that is coupled to the photon detector 32. By way of example, the focusing lens 26 can have a focal length of approximately 81 mm and the optical fiber 30 can be a multimode optical fiber having a diameter of approximately 100 μm. In some embodiments, the photon detector 32 is an avalanche photodiode (APD). By way of example, the photon detector 32 can be a Perkin-Elmer SPCM-AQR-13-FC. This APD has a typical dark-count rate of 250 cps and a dead-time of 50 ns.

Transistor-transistor logic (TTL) output pulses from the photon detector 32 (e.g., at >2.5 V, 35 ns wide) can be fed into a counter/timer board 34 (e.g., USB-6210, National Instruments) that is connected to an interface (e.g., USB interface) of a computing device 36, such as a personal computer. Software provided on the computing device 36 can then be used to process the data acquired by the system hardware to determine the dimensions of nanoparticles. By way of example, the software can comprise custom functions and/or algorithms written for Igor Pro data acquisition and processing software (Wavemetrics, Lake Oswego, Oreg.).

Figure 2:
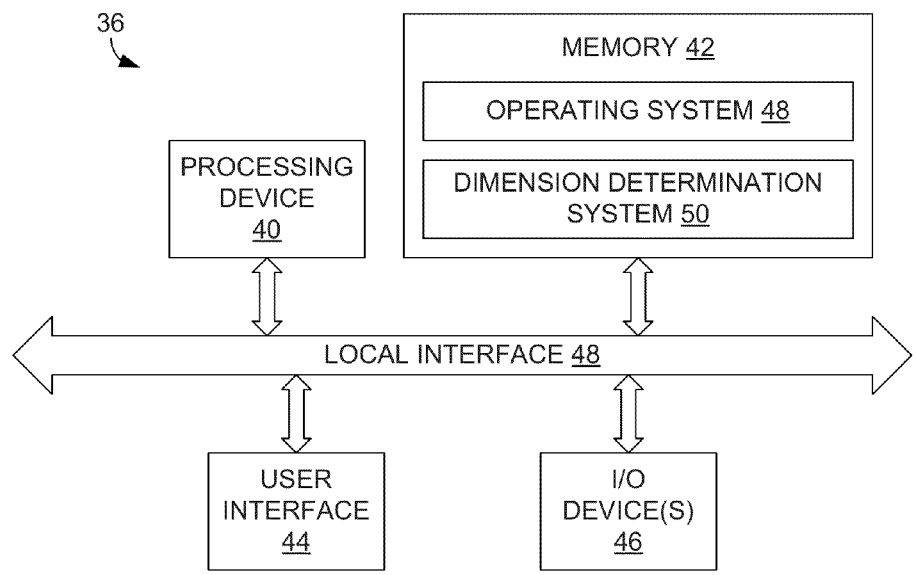
FIG. 2 is a block diagram of an embodiment of a computing device shown in FIG. 1.

FIG. 2 illustrates an example configuration for the computing device 36 shown in FIG. 1. As noted above, the computing device 36 can take the form of a personal computer. It is noted, however, that the computing device 36 can take other forms. For example, the computing device 36 could be configured as a tablet computer, a smart phone, or any other device that has computing and display capabilities.

In the example of FIG. 2, the computing device 36 includes a processing device 40, memory 42, a user interface 44, and at least one I/O device 46, each of which is connected to a local interface 48. The processing device 40 can include a central processing unit (CPU) or a semiconductor-based microprocessor (in the form of a microchip). The memory 42 includes any one of or a combination of volatile memory elements (e.g., RAM) and nonvolatile memory elements (e.g., hard disk, ROM, Flash, etc.). The user interface 44 comprises the components with which a user interacts with the computing device 36, such as a keyboard, keypad, and a display screen, and the I/O devices 46 are adapted to facilitate communications with other devices.

The memory 42 (a non-transitory computer-readable medium) comprises programs (logic) including an operating system 48 and a nanoparticle dimension determination system 50. The dimension determination system 48 includes one or more functions and/or algorithms that are configured to receive data measured by the system hardware and make determinations as to the dimensions of nanoparticles in the sample under evaluation by the system 10. As described below, the determinations can comprise determining an average aspect ratio of the nanoparticles based upon diffusion measurements obtained by the system 10. Described below are experiments that were performed using a system similar to system 10 to evaluate how well the system can estimate nanorod aspect ratios from such diffusion measurements.

Photon Counting and Processing

Photon counting and processing utilizes a TTTR approach. To obtain the TTTR photon count history, the TTL output from the photon detector was used as the gate input for the internal clock of the counter/timer board running either at 20 or 80 MHz. The raw TTTR data was streamed and stored directly to a computer hard disk for subsequent off-line processing. To avoid data overflow, individual measurement segments were limited to a total of $5 \times 10^5$ photon arrivals before data were stored in individual files on the computer hard disk. Extended measurement durations were obtained by simply concatenating individual measurement segments.

Gold Nanorod Samples and DDLS Measurements

Gold (Au) nanorods with nominal dimensions of 45 nm length×10 nm diameter (prod. #30-10-850; lot R01141B1) and 135 nm length×20 nm diameter (prod #30-HAR-1064; lot #RPB049 and prod #30-HAR-1000; lot #HAR 95) were purchased from Nanopartz, Inc. (Loveland, Ohio). Au rod dimensions were chosen so that, in principle, the intrinsic absorption of the Au nanorods was near a minimum at the laser wavelength of $\lambda=633$ nm used for light scattering experiments (see FIG. 4). Subsequently, the three different samples are referred to by the respective peaks in their absorption spectra (FIG. 4) as Au 823 (45×10 nm sample), Au 855 (135×20 nm, 30 HAR 1064), and Au 953 (135×20 nm, 30-HAR 1000). For DDLS measurements, Au stock solutions were diluted 3- to 6-fold into deionized water containing 0.1% of the stabilizing detergent cetyl trimethylammonium bromide (CTAB) as a stabilizing agent (Fisher Scientific, Pittsburgh, Pa.). The solvent was filtered through 0.22 μm polytetrafluoroethylene (PTFE) syringe filters before mixing with the Au nanorods. Solutions were centrifuged at 1,400 rpm and 30° C. for 15 minutes to remove any undissolved aggregates or trapped air bubbles. Relative Au rod concentrations for solutions were characterized using sample absorbance determined at $\lambda=633$ nm with a UV spectrophotometer (ThermoElectron Corp.).

DDLS and DLS Measurements of Au Samples

For dynamic light scattering (DLS) measurements, Au solutions were transferred to clean 10 mm glass cuvettes and placed in a thermostated sample holder. DDLS measurements were performed using a custom-built 90° scattering setup similar to that described above, which yielded a scattering vector q of $1.87 \times 10^7$ m$^{-1}$ or 1/(53.6 nm) for n=1.33, $\lambda=633$ nm. Polarized (v-v) and depolarized (v-h) TTTR photon counts were accumulated for durations ranging from 90 sec (v-v) to 20 min (v-h), using collection apertures of 1 mm (v-v) or 2 mm (v-h), respectively. The corresponding correlation functions were calculated using custom programs written in a C-language hybrid (Igor programming language). In addition, a commercial DLS light scattering unit (Nanosizer S, Malvern Instruments) using a backscattering geometry ($\theta=173°$) was used to derive distributions of relaxation rates and to collect data at a different scattering wave vector ($q=2.68 \times 10^7$ m$^{-1}$ or 1/(37.9 nm) for n=1.33, $\lambda=633$ nm). All measurements were performed at 30° C. to maintain CTAB solubility.

Optical Absorbance and TEM Measurements

All optical absorbance measurements were performed using a UV-1 spectrophotometer from Thermo Electron Corp. Au nanorod stock solutions were diluted into 0.1% CTAB/water solvent solutions until absorbance was less than 0.5. All absorbance readings were corrected for any background contributions from the solvent. Beyond 1050 nm, spectral readings were not very reliable.

Transmission electron microscopy (TEM) measurements were performed using a Tecnai T20 G2 transmission electron microscope run at 200 kV AC. Ten microliters of 10 to 100× fold diluted Au samples were deposited on sample grids, dried with dry nitrogen, and then introduced into the vacuum chamber for imaging.

Custom DDLS Setup Using TTTR Photon Counting

One of the practical challenges faced when using DDLS is the notoriously low photon count rates associated with depolarized light scattering signals. Using gaussian statistics to approximate photon counting noise ($S/N \propto 1/\sqrt{N}$), it is estimated that about N=400 photons are needed to achieve a modest 5% noise level for a given decay channel. For the comparatively strongly scattering Au nanorods used in the experiments, typical depolarized count rates are around $f_N=10^4$ cps (see FIG. 3A). For rotational decay rates $\Gamma$ as high as 100 kHz, the system only accumulates $f_N/\Gamma=0.1$ cps in that decay channel. To reach the modest 5% signal-to-noise level, the signal is accumulated for 400/0.1 s≈1 hr. Hence, efficient processing and counting of scattered photons is essential.

To address this concern, a custom DDLS system using TTTR photon counting was used. As noted above, the optical design of the system uses 90° light scattering. Notably, however, photon counting and processing departs in two significant ways from traditional 90° light scattering setups. First, instead of counting the number of photons arriving within fixed time bins, the temporal sequence of photon arrival times is labeled using the TTTR scheme commonly used for low-intensity fluorescence life-time measurements. To obtain the TTTR photon count history, the TTL output from the photon detector is used as the gate input to the internal clock of a counter/timer board with either 20 or 80 MHz resolution. Hence, photon counts are recorded as a series of delay times between subsequent photon events. This dramatically diminishes the large overhead of empty time bins common for time-binned data at low count rates and, therefore, the acquisition times required to accumulate DDLS correlation functions. As a result, the corresponding demands on bus speeds for data transfer and on space for data storage, as well as the computational time required to calculate the correlation function, is reduced.

The second difference in photon count processing is that the raw TTTR data are subjected to preprocessing prior to calculation of the intensity correlation functions. One immediate advantage of acquiring the raw photon count history is the ability to eliminate photon bursts due to large aggregates or air bubbles, which otherwise distort the correlation functions derived from weak v-h signals. Again, given the extended acquisition times needed for such measurements, even weak contamination by dust and air bubbles will distort correlation functions during acquisition periods as short as one minute. This is shown in FIG. 3A for a short photon count history from an Au nanorod sample. Even after filtration and centrifugation, the sample displayed significant burst events. The bursts are likely due to air bubbles, the formation of which is facilitated by the presence of the CTAB surfactant required to keep Au nanorods in suspension. As indicated in FIG. 3B, these burst events induce long, slow relaxation components and distort the baseline in the corresponding correlation function. These effects were removed by restricting the deviations from the mean count rate in the photon count history to approximately three standard deviations and by concatenating the resulting disjointed segments of the raw TTTR vector of arrival times. For the bimodal decays that were encountered, the effect of bursts on the fast relaxation component was quite modest (221 versus 226 kHz) but, upon removal of spurious counts, the slow relaxation component decreased from 5.4 to 4.1 kHz and the correlation function approached a well-defined baseline (FIG. 3C). For weak depolarized light scattering signals, these manipulations of count rate histories are much more efficiently performed using TTTR photon counts.

An added advantage of the custom system is the control over the solid angle used to collect the weak v-h scattering signals. For a 1 mm aperture in the system, only a single coherence area of scattered light is collected. The resulting A/B ratio of the experimentally observed intensity correlation function $G_2(\tau)$, i.e., the ratio of $(G_2(0)-G_2(\infty))/G_2(\infty)$, is near its theoretical limit of 1. However, the resolution of the various relaxation rates contributing to $G_2(\tau)$ contained within the weak depolarized scattering signals is typically not limited by the A/B ratio but by several other factors. These include the intrinsic shot noise of the scattering signal, the contributions from photon detector dark counts to the signal, and the presence of spurious counts arising from larger impurities. The first two of these latter noise limitations can be significantly diminished by increasing the total flux of scattered photons regulated by the iris diaphragm. To reduce spurious bursts from large impurities, meticulous filtering and cleaning of the sample solutions are required. As discussed above, acquisition and preprocessing of raw photon counts help to reduce this latter problem further. All DLS and DDLS light scattering measurements at 90° were performed using the above custom light scattering setup.

Optical Absorption Spectra of Au Nanorod Samples

Figure 4:
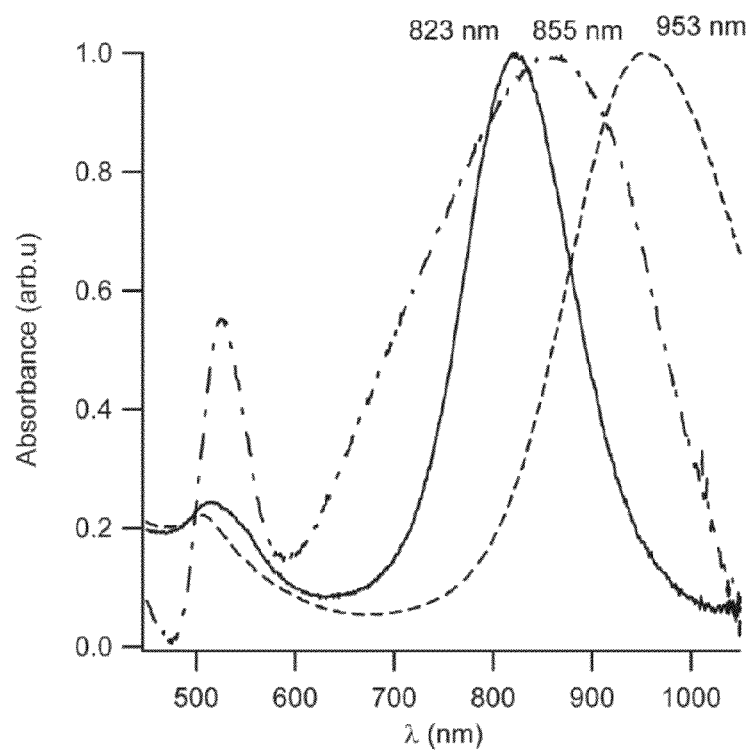
FIG. 4 is a graph that illustrates optical absorption spectra of Au nanorods.

The absorption peaks arising from longitudinal surface plasmon resonance (LSPR) are often used to obtain an estimate of the geometric aspect ratio AR=L/d for metallic nanorods, where L and d are the length and diameter of the nanorods, respectively. To minimize absorption effects on the scattering measurements, Au nanorod dimensions were selected that are likely to produce minima in their absorption spectra near the HeNe wavelength ($\lambda$=633 nm) used for light scattering measurements. The absorption spectra of the three specific Au nanorod sample lots used in the experiments were confirmed (FIG. 4). The transverse (TSPR) and longitudinal (LSPR) surface plasmon resonance peaks for the 45×10 nm sample were near 515 nm and 823 nm, respectively, with an absorbance minimum near 630 nm. This minimum indeed coincided with the wavelength of the HeNe laser. The absorption spectra for the two nominally similar 135×20 nm samples were dramatically different from each other, with LSPR maxima at 855 nm and 953 nm, respectively. It is notable that the spectrum with the 855 nm peak also deviated significantly from the quality control spectrum provided by the manufacturer. The three specific sample lots were identified by their actual LSPR peaks as Au-823, Au-855, and Au-953. The nominal aspect ratios and rod diameters quoted by the manufacturer were AR=4.3, d=10 nm (Au-823); AR=5.8, d=14 nm (Au-855); and AR=6.6, d=20 nm (Au-953), respectively. As detailed further below, independent electron microscopy measurements on the specific batches used in the experiments yielded quite different results for dry nanorod dimensions with AR=3.5, d=12 nm (Au-823); AR=2.7, d=41 nm (Au-855); and AR=5.7, d=8 nm (Au-953), respectively.

Polarized and Depolarized Intensity Correlation Functions for Au Nanorods

Figure 5:
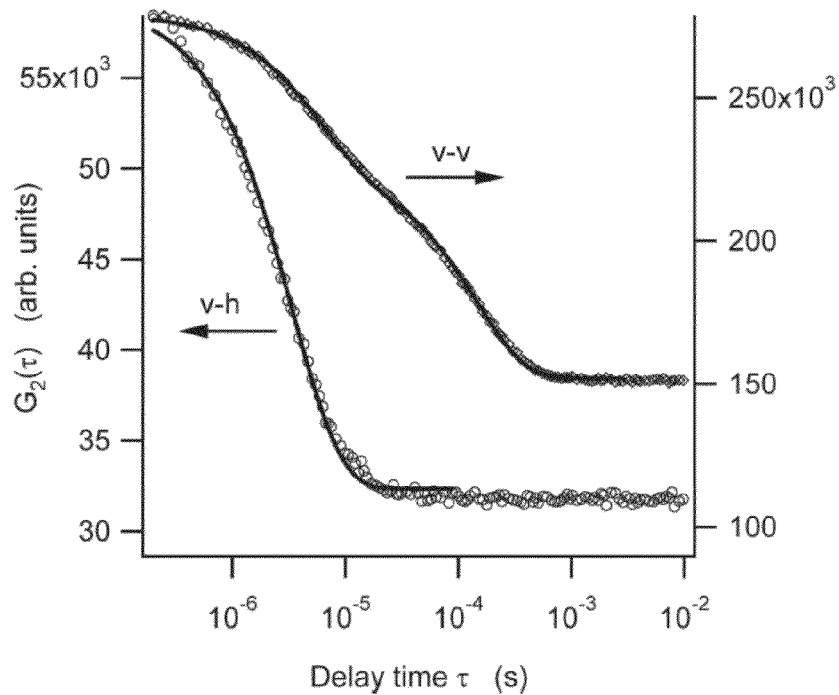
FIG. 5 is a graph that illustrates polarized and depolarized correlation functions of Au nanorods in solution.

FIG. 5 displays typical unnormalized polarized (v-v) and depolarized (v-h) intensity correlation functions obtained for the 43×10 nm Au nanorod solution (Au-823). It is immediately apparent that the depolarized correlation function $G_{2,v-h}(\tau)$ decays significantly faster than the polarized correlation function $G_{2,v-v}(\tau)$. In addition, the decay of the v-h correlation function appears nearly mono-modal while the v-v decay contains at least two distinct relaxation rates.

The solid lines through the intensity correlation functions in FIG. 5 were obtained by directly fitting the raw intensity correlation functions to the square of either a single- or double-exponential function with adjustable offset, i.e., $$G_{2,v-h}(\tau) = (A \exp^{-(\Gamma_{tr}+\Gamma_{rot})\tau})^2 + B \quad (1)$$

and $$G_{2,v-v}(\tau) = (A_1 \exp^{-\Gamma_{tr}\tau} + A_2 \exp^{-(\Gamma_{tr}+\Gamma_{rot})\tau})^2 + B. \quad (2)$$

Figure 6:
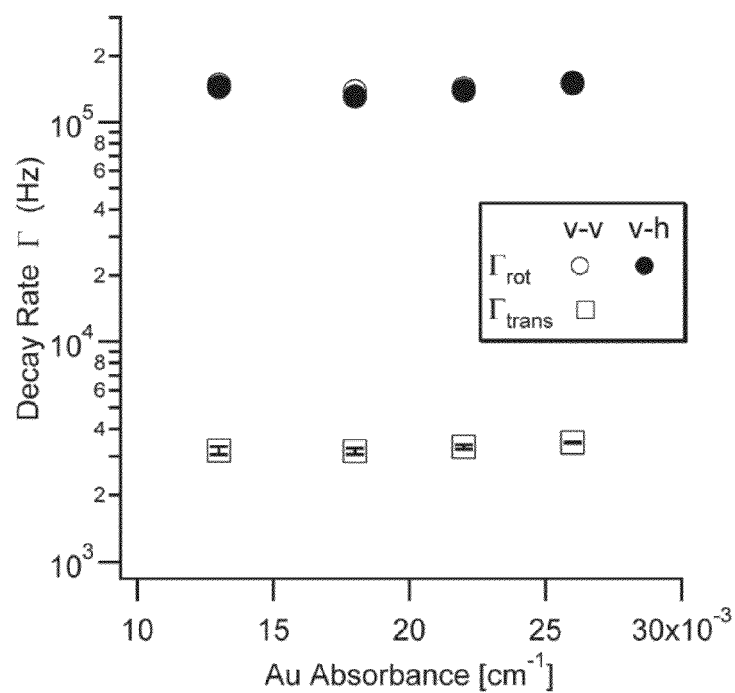
FIG. 6 is a graph that illustrates lack of concentration dependence of relaxation rates.

In the fits, the amplitudes A and B and the relaxation rates $\Gamma_{tr}$ and $\Gamma_{rot}$ are adjustable parameters. To determine whether residual effects of Au nanorod absorption or the presence of interparticle interactions among the charged nanorods might affect relaxation rates at our sample concentrations, DDLS measurements were repeated for a series of progressive sample dilutions. As shown in FIG. 6, the translational and rotational relaxation rates $\Gamma_{tr}$ and $\Gamma_{rot}$ for the shorter nanorods had no discernable dependence on Au nanorod concentration. Hence, within the measured concentration range, the effects of Au absorption or particle-particle interactions on nanorod diffusion are negligible. Decay rates for the longer nanorod samples did show a very weak but systematic increase of their decay rates with concentration, consistent with either weak hydrodynamic or electrostatic repulsion (data not shown). To derive the corresponding relaxation rates in the absence of interactions, the experimental rates were linearly extrapolated to their infinite dilution limits (C=0) prior to analysis.

The experimental relaxation rates are related to the translational and rotational diffusion rates $D_{tr}$ and $D_{rot}$ via $$\Gamma_{tr} = D_{tr} q^2 \quad (3)$$

$$\Gamma_{rot} = 6 D_{rot}. \quad (4)$$

Figure 7:
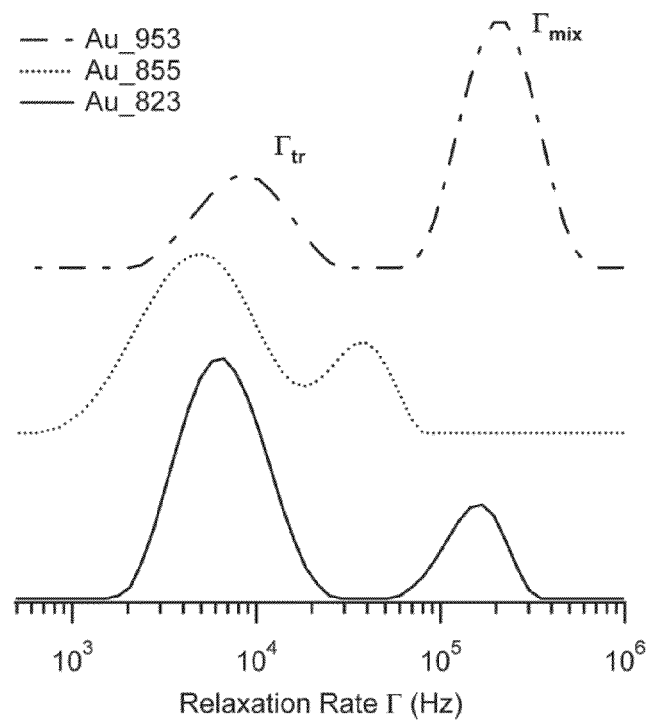
FIG. 7 is a graph that illustrates a distribution of relaxation rates for Au nanorods.

The magnitude of the wave vector q in Equation (3) is given by $$q = (4\pi n/\lambda) \sin(\theta/2) \quad (5)$$

where n is the refractive index of the solution, $\lambda$ the wavelength of the incident light, and $\theta$ is the scattering angle between the incident and scattered light directions. The value for the wave vector in the DDLS setup was $q=1.87\times10^7$ m$^{-1}$ or 1/(53.6 nm). Usually, measurements at multiple angles are required to separate the (q-dependent) translational and (q-independent) rotational relaxation components. This dependence is typically rather weak over the range of experimentally accessible q-values, making the separation a non-trivial and time consuming endeavor. Separate v-v and v-h measurements, instead, readily identify the translational and mixed translational/rotational relaxation components (FIG. 5). The translational and rotational relaxation rates, $\sigma_{tr}$ and $\Gamma_{rot}$ obtained from single- or double-exponential fits to the raw intensity correlation functions from polarized (v-v) and depolarized (v-h) DDLS measurements are summarized in Table 1. In addition, a commercial DLS unit was used without polarizers that essentially collects v-v data. Due to the back-scattering geometry of the DLS setup ($\theta=173°$), the corresponding value for the wave vector was $q=2.64\times10^7$ m$^{-1}$ or 1/(37.9 nm). These latter measurements yielded bimodal distributions of relaxation rates with two well-defined peaks (FIG. 7). Based on the identification of relaxation peaks from DDLS, the faster of the two decay rates could be assigned to $\Gamma_{mix} = \Gamma_{tr} + \Gamma_{rot}$ and the slower one to $\Gamma_{tr}$. Table 1 provides a summary of the peak values for the experimental decay rates measured for the three different Au samples. Consistent with the $q^2$-dependence of $\Gamma_{tr}$ (Equation 3), the translational relaxation rates at q=173° are about twice as fast than those at 90°. As expected from Equation (4), the rotational relaxation rates, $\Gamma_{rot} = \Gamma_{mix} - \Gamma_{tr}$, are essentially independent of the scattering angle.

TABLE 1

DDLS and DLS Measurements of Au Nanorods Relaxation Rates

| Sample | $\Gamma_{tr}$ (kHz)[a] | $\Gamma_{rot}$ (kHz)[a] | $\Gamma_{rot}$ (kHz)[b] | $\Gamma_{tr}$ (kHz)[c] | $\Gamma_{mix}$ (kHz)[c] |
|---|---|---|---|---|---|
| Au_823 | 3.27 ± 0.13 | 145.7 ± 4.2 | 138 ± 8.1 | 6.44 | 163 |
| Au_855 | 2.07 ± 0.35 | 23.8 ± 1.5 | 17 ± 0.65 | 4.96 | 37.7 |
| Au_953 | 4.09 ± 0.14 | 212.2 ± 0.8 | 189 ± 6.3 | 8.68 | 215 |

[a] from DDLS measurements at $\theta = 90°$; v-v polarization; double-exponential fit
[b] same as [a] but using v-h polarization
[c] from DLS measurements at $\theta = 173°$; relaxation rates are from peak of log-normal size distribution Unified Data Analysis of Translational and Rotational Au Nanorod Diffusion A goal of the subsequent data analysis is to relate these experimental relaxation rates to the corresponding geometrical parameters (length L and aspect ratio AR) of the nanorods in their solution environment via comparison to theoretical predictions for translational and rotational diffusion of either straight cylinders or prolate ellipsoids. Previous reports on translational and rotational diffusion of elongated metallic nanoparticles could not fully resolve discrepancies between experimentally measured and theoretically predicted diffusion rates. One of the challenges of the data analysis is to find the best match of two experimental parameters ($\Gamma_{tr}$ and $\Gamma_{mix}$) to the predictions for the rotational and translational diffusion which, in turn, depend non-linearly on two underlying geometrical parameters (e.g., L and AR). One approach has been to use the adjustable geometrical parameters (L and AR) in order to match one set of data (e.g., rotational relaxation) and see whether this provided reasonable agreement for the other data set (e.g., translation). For example, the inclusion of a detergent layer of CTAB in theoretical calculations was suggested in order to match rotational diffusion data, but noticeable deviations from translational diffusion rates remained. A more rational approach that was suggested involves using the ratio of the translational and the cube-root of the rotational diffusion coefficients to obtain an estimate for a function f(AR) that is only dependent on AR. That function could be numerically calculated and inverted to determine AR directly. This approach was used to determine the dimensions of short DNA oligonucleotides. While the proposed specific ratio is mathematically exact, the resulting dependence of f(AR) on AR is rather weak, varying by less than a factor of 2 for aspect ratios AR ranging between 2 and 20.

Figure 8:
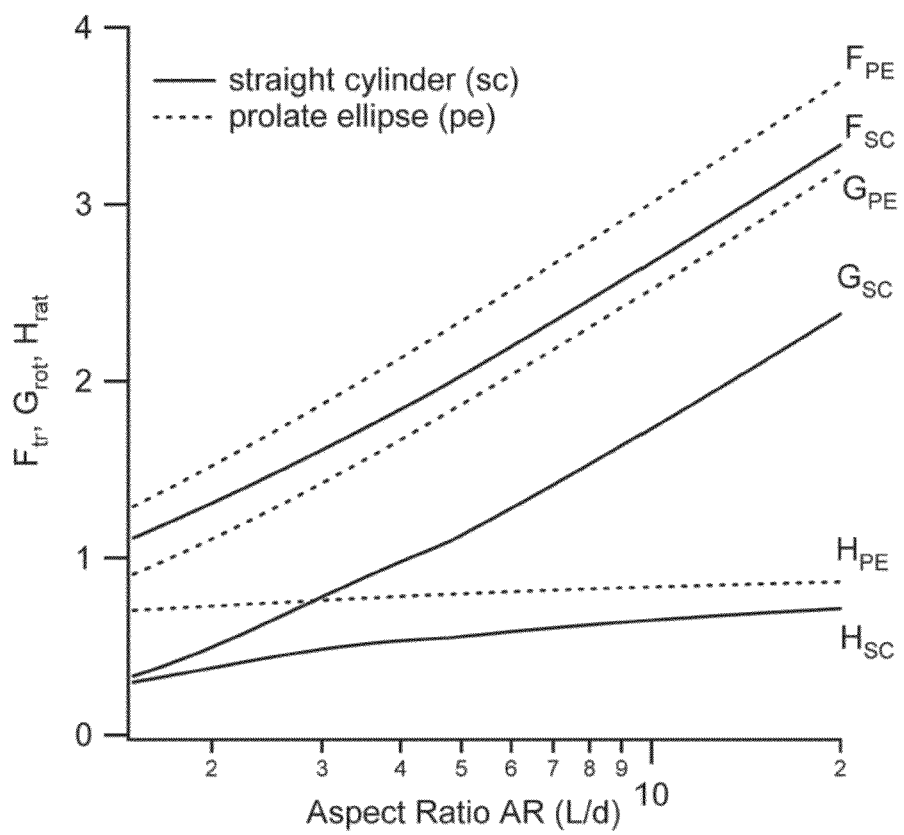
FIG. 8 is a graph that illustrates the dependence of translational and rotational diffusivities on the aspect ratio for either cylindrical rods or prolate ellipsoids.

The analysis methodology disclosed herein combines the two experimentally measured relaxation rates, $\Gamma_{tr}$ and $\Gamma_{mix}$, into a single ratio. As shown below, this ratio can be used to extract the overall length L for the nanorods which, in turn, allows extraction of the corresponding aspect ratio AR. It was determined that the ratio $(\Gamma_{mix} - \Gamma_{tr})/\Gamma_{tr}$ of the experimentally observed relaxation rates serves this purpose. The starting point for the analysis is the expressions for translational and rotational diffusion coefficients, $D_{tr}$ and $D_{rot}$, using two different geometrical models of elongated nanoparticles: straight cylinders and prolate ellipsoids. In the following discussion, L is the length (major diameter) of the cylindrical (ellipsoidal) nanoparticle, d is the (minor) diameter and AR=L/d is the cylinder's or ellipsoid's aspect ratio. Predictions for straight cylinders use extrapolating polynomials derived by de la Torre et al. from simulation results with the bead-shell model. These extrapolations are valid for aspect ratio AR between 2 and 20 and, more recently, for AR values down to 0.1. Expressions for prolate ellipsoids date back to closed-form expressions obtained by Perrin. The theoretical expressions for the translational diffusion constants are of the form $$D_{tr}=(k_B T/3\pi\eta L)F(AR) \quad (6)$$

where F(AR) is a model-dependent function of the aspect ratio given by straight cylinder $F_{SC}(AR)=\ln(AR)+0.312+0.565/AR-0.1/AR^2$ (7a)

$$F_{SC}(AR) = \sqrt[3]{\frac{2}{3}AR^2}\,(f/f_0)^{-1} \quad (7b)$$

with $f/f_0=1.009+0.01395\ln(AR)+0.0788\ln(AR)^2+0.006040\ln(AR)^3$
and for prolate ellipsoid $$F_{PE}(AR)=AR\times S(AR) \quad (8)$$

with $S(AR)=\ln[AR+\sqrt{AR^2-1}]/\sqrt{AR^2-1}$
The corresponding expressions for rotational diffusion are $$D_{rot}=(3k_B T/\pi\eta L^3)G(AR) \quad (9)$$

where G(AR) is given by straight cylinder $G_{SC}(AR)=\ln(AR)-0.662+0.917/AR-0.05/AR^2$ (10a)

$$G_{CS}(AR) = \frac{2}{9}AR^2(\tau/\tau_0)^{-1} \quad (10b)$$

with the above ratio of rotational relaxation times $\tau/\tau_0$ given by $\tau/\tau 0=1.18+1.116(\ln(AR)+0.2877)^2-0.9729(\ln(AR)+0.2887)^3+0.4954(\ln(AR)+0.2877)^4$ and for prolate ellipsoid $$G_{PE}(AR)=1/2AR^2[((2AR^2-1)/AR)S(AR)-1]/(AR^2-1) \quad (11)$$

where S(AR) was defined in Equation (8). The two separate equations for F(AR) and G(AR) (7a and b and 10 a and b) cover different ranges of AR, with AR=2–20 and AR=0.1–20, respectively. It was determined that the two extrapolation polynomials agreed well in the overlap region of AR=2–5, but that Equation (10b) developed an unphysical undulation for AR>5. This is probably due to the paucity of data points for large AR used to derive the extrapolation polynomials for $f/f_0$ and $\tau/\tau_0$. In the analysis a switch was therefore made from equations (7b/10b) to (7a/10a) for AR>5. Plots for F(AR) and G(AR) for both models are shown in FIG. 8.

The experimentally derived values for $\Gamma_{rot}$ (or $\Gamma_{mix}$) and $\Gamma_{tr}$ can then be combined into the simple ratio $\Gamma_{rot}/\Gamma_{tr}=(F_{mix}-F_{tr})/\Gamma_{tr}$. The relaxation rates are related to the corresponding diffusion constants via $\Gamma_{tr}=D_{tr}q^2$ and $\Gamma_{mix}=6D_{rot}+D_{tr}q^2$ (see Equations 3-5), where q is the scattering vector given in Equation (5). Hence $\Gamma_{rot}/\Gamma_{tr}=(\Gamma_{mix}-\Gamma_{tr})/\Gamma_{tr}=(6/q^2)(D_{rot}/D_{tr})=54H(AR)/(Lq)^2$, which follows from Equations (6) and (9) and by defining $H(AR)=G(AR)/F(AR)$. Importantly, because both G(AR) and F(AR) have very similar AR dependencies, their ratio H(AR) is nearly constant for either cylinders or ellipsoids (see FIG. 8). Interestingly, the value of H(AR) is also rather insensitive to the specific theoretical model used to analyze the data (here, straight cylinders or prolate ellipsoids). As a result, the ratio of decay rates $\Gamma_{rot}/\Gamma_{tr}$ is strongly dependent on the overall length L of the nanoparticle but only varies weakly with the aspect ratio AR. Both factors represent significant advantages for obtaining robust estimates for L. The nanoparticle length L can therefore be expressed as $$L=q^{-1}\sqrt{54(\Gamma_{rot}/\Gamma_{tr})^{-1}H(AR)} \quad (12)$$

Using Equation (6), the estimates obtained for L can then be used to determine F(AR)

$$F(AR)(3\pi\eta/k_B T)(\Gamma_{tr}L/q^2) \quad (13)$$

Equations (12) and (13) represent the basic approach towards converting the experimental relaxation rates into values for nanoparticle length L and aspect ratio AR. The results obtained for F(AR) can be used in two ways. First, the specific values for F(AR) derived from Equation (13) need to fall within the range predicted from the theoretical model. This indicates whether the underlying geometrical model (straight cylinder or ellipsoid) can possibly match the actual nanorod geometry. By tabulating F(AR) versus AR, this relationship can then be inverted to obtain actual predictions for the aspect ratio AR.

Au Nanorod Length and Aspect Ratios Determined from DDLS and DLS

Using the relaxation rates in Table 1, the corresponding ratios $\Gamma_{rot}/\Gamma_{tr}$ or $(\Gamma_{mix}-\Gamma_{tr})/\Gamma_{tr}$ listed in Table 2 were determined. Estimates for the corresponding Au nanorod length L from Equation (12) were derived using the $\Gamma_{rot}/\Gamma_{tr}$ ratio from the v-v measurements obtained from DDLS measurements. Results using either the v-h measurements or the DLS measurements taken with a commercial unit yielded comparable results. Equation (12) was evaluated for each of the three Au nanorod samples, and for either straight cylinders ($L_{SC}$) or prolate ellipsoids ($L_{PE}$). Values for H(AR) were taken either for AR=2.5 or AR=4, which we consider the limits of reasonable estimates for the nanorods' AR given their original specifications. The range of values for the overall length L represents those obtained for H(2.5) and H(4), respectively. Using Equation (13), the corresponding range of values for F(AR) for either straight cylinders or prolate ellipsoids was then determined. The results of these calculations are summarized in Table 2 as well. While the estimates for the overall nanorod length are different between the two models, they are both reasonable (see also TEM analysis below). However, the values for F(AR) derived from these models fall outside the range of theoretical values obtained for either straight cylinders or prolate ellipsoids. The same result was obtained with each of the three Au nanorod samples that were investigated.

TABLE 2

Theoretical Predictions of Rod Length L and Translational Modulation Factor F(AR)

| Sample | $\Gamma_{rot}/\Gamma_{tr}$[a] | $\Gamma_{rot}/\Gamma_{tr}$[b] | $(\Gamma_{mix}-\Gamma_{tr})/\Gamma_{tr}$[c] | $L_{SC}$ (nm)[d] | $F_{SC}$[e] | $L_{PE}$ (nm)[d] | $F_{PE}$[e] |
|---|---|---|---|---|---|---|---|
| Au_823 | 44.6 | 42.2 | 24.3 | 39-43 | 0.65-0.72 | 52-53 | 0.85-0.87 |
| Au_855 | 11.5 | 8.2 | 6.6 | 77-85 | 0.82-0.90 | 100-103 | 1.07-1.10 |
| Au_953 | 51.9 | 46.2 | 23.7 | 36-41 | 0.76-0.87 | 47-48 | 1.05-1.08 |

[a]$\Gamma_{rot}$(vv)/$\Gamma_{tr}$(vv) (DDLS)
[b]$\Gamma_{rot}$(vv)/$\Gamma_{tr}$(vh) (DDLS)
[c]from DLS
[d]using $\Gamma_{rot}$(vv)/$\Gamma_{tr}$(vv) from first column in Equation (12) and $H_T$(AR) for AR = 2.5 and 4. Results using data from second or third column are within 2-3 nm.
[e]using Equation (13) and $H_T$(AR) at AR = 2.5 and 4

Characterizing Sample Polydispersity

Figure 9A:
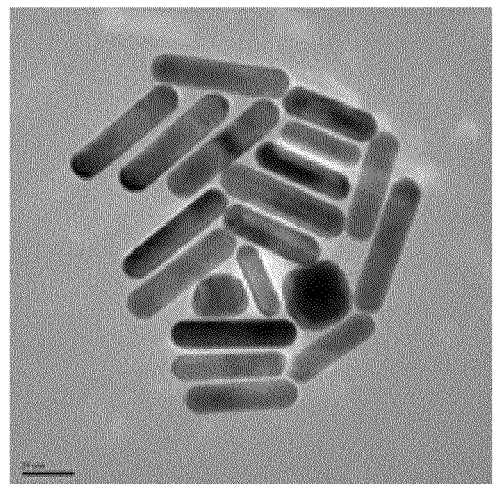
FIGS. 9A-9C are electron micrographs of Au nanorod samples.
Figure 9B:
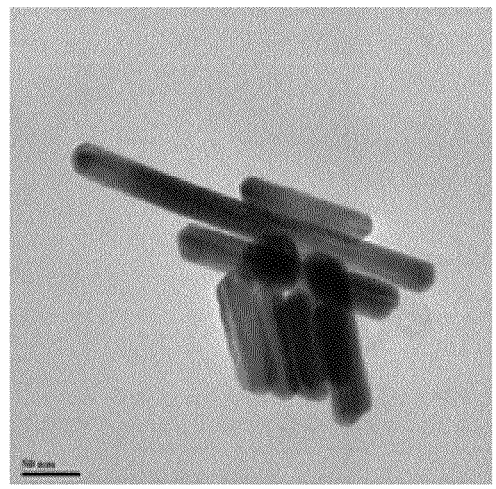
Figure 9C:
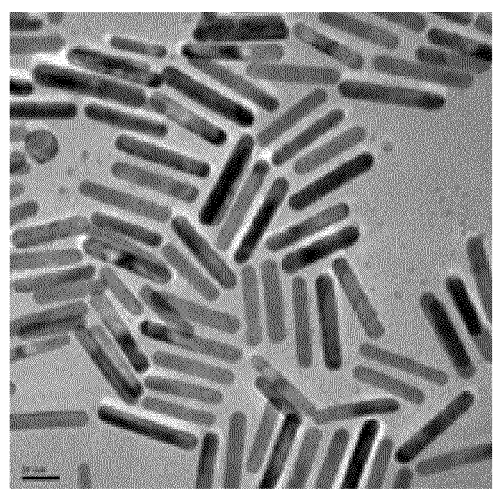

One potential reason for the observed mismatch between the theoretical predictions and experimental results could be the intrinsic polydispersity of the sizes and shapes of the nanorod samples. Using transmission electron microscopy, the actual dimensions and shapes for each of the three Au nanorod samples in these experiments were determined (FIG. 9). The dimensions for the Au-823 samples were reasonably uniform and close to their specifications but did contain some more compact aggregates with AR ratios closer to 1 (FIG. 9A). The higher aspect nanorods (Au-855) were noticeably more polydisperse both in their physical dimensions and their morphologies. For example, the longest nanorod in FIG. 9B measured about 310×27 nm, compared to the average of 135×20 nm quoted by the manufacturer. Finally, the last batch of Au-953 was reasonably homogeneous, but significantly shorter and thinner (L=40-50 nm, d=5-7 nm) than indicated by the manufacturer's specification sheet.

In order to assess sample polydispersity from the distribution of decay rates of the light scattering signal, the built-in Laplace inversion algorithms of the commercial DLS unit were utilized. Laplace inversion converts the field correlation function into distributions of decay rates instead of the two discrete decay rates used for the analysis of the DDLS intensity correlation functions. The Laplace inversion algorithm returns a distribution of hydrodynamic diameters for spherical particles diffusing at the same rate as the measured relaxation rates. To convert these diameters D back into the underlying distribution of relaxation rates, one simply combines Equation (4) with the standard Stokes-Einstein relation (Equation (6) with D equal to L and F(AR)=1), to obtain $$\Gamma=(k_B T/3\pi\eta)q^2/D \qquad (14)$$

As mentioned above, the two peaks in the distributions of relaxation rates arise from the (slower) translational ($\Gamma_{tr}$) and (faster) mixed modes ($F_{mix}=\Gamma_{tr}+\Gamma_{rot}$) (see FIG. 7). The more heterogeneous sample Au-853 displays a significantly broader translational peak, particularly when accounting for the logarithmic scale of the relaxation rate axis. However, the maximal relaxation rates for $\Gamma_{tr}$ and $\Gamma_{mix}$ for both peaks closely match those returned by the simplified double-exponential fit to the v-v correlation functions obtained with the DDLS setup. Hence, the large variety of both shapes and sizes present in the Au-855 sample also appears in the broad distribution of relaxation rates seen with DLS. However, both the Au-823 and Au-953 samples were sufficiently homogeneous to permit a meaningful comparison between the theoretical models and the experimental results. Table 3 summarizes the dimensions of the Au nanorods as provided by the manufacturer, direct results of TEM measurements and the lengths L of the rods derived from DDLS measurements and our analysis, assuming either straight cylinders or prolate ellipsoids as geometrical models.

TABLE 3

Au Nanorod Dimensions: TEM vs. DDLS

| Sample | L × d (nm)[a] nominal | AR[b] LSPR | L × d (nm) TEM | AR[c] TEM | L (nm)[d] DDLS |
|---|---|---|---|---|---|
| Au_823 | 43 × 10 | 4.3 | 42 × 12 | 3.5 | 41/53 |
| Au_855 | 132 × 20 | 6.6 | 111 × 41 | 2.7 | 81/102 |
| Au_953 | 81 × 14 | 5.8 | 46 × 8 | 5.7 | 39/48 |

[a]specifications for sample lot provided by the manufacturer
[b]estimate of manufacturer based on LSPR peak value
[c]measurement from TEM images of actual sample lots
[d]average length taken from Table 2 for (straight cylinder/prolate ellipsoid)

Discussion of the Results

Depolarized and polarized dynamic light scattering were used to determine the translational and rotational relaxation rates for three commercial samples of faceted Au nanorods. Polarized and depolarized measurements provided comparable decay rates for the rotational diffusion coefficient. However, the use of depolarized light scattering allowed immediate identification of the rotational relaxation component. The results from our custom DDLS setup agreed quantitatively with relaxation rates obtained with a commercial DLS unit in backscattering geometry.

A new unified approach for directly deriving particle dimensions from translational and rotational relaxation rates was proposed, using different models for the particle geometry. In particular, considered were theoretical predictions for straight cylinders and prolate ellipsoids. Specifically, Equation (12) provides a direct way to extract the overall length (long dimension) of elongated nanoparticles from the ratio of rotational and translational relaxation rates. Table 3 indicates that, with the exception of the highly polydisperse sample Au-853, the overall lengths of the nanorods predicted from either the straight cylinders or prolate ellipsoids model agreed fairly closely with each other and with the results of direct TEM measurements. In contrast, the values for F(AR) derived from Equation (13) fell outside the range of meaningful values for either of the two geometrical models. Using the derived values for L to determine G(AR) instead of F(AR) yielded comparable discrepancies with experimental values for G(AR) that were too small for physically plausible AR ratios. The TEM measurements and the analysis of sample polydispersity indicate that this discrepancy, with the possible exception of the Au-853 sample lot, is unlikely to be due to heterogeneities in Au rod dimensions or geometry. It is notable that the approach taken by Rodriguez-Fernandez et al. of directly matching the rotational diffusion data to model predictions for cylinders was attempted. As they observed, this required the assumption of an adsorbed CTAB layer in the theoretical calculation to obtain a reasonable match. There are several reasons why this assumption is not consistent with our data. First, as these authors have observed, values of L and AR could not be found that would provide simultaneously good fits to both translational and rotational diffusion constants. More importantly, the revised analysis indicates that the actual length predicted by the straight cylinder geometry is close to the bare nanorod dimensions, in direct contradiction to the idea of a rigid CTAB layer.

The inability of either the straight cylinder or the prolate ellipsoid model to provide reasonable estimates for the aspect ratios of the nanorods is particularly intriguing. The TEM images suggest some possible explanations for this discrepancy. The actual geometry of gold nanorods shows protruding, faceted end caps and clearly faceted sides. Hence, actual nanorod geometries are distinct from either prolate ellipsoids or straight cylinders with flat endcaps. Sensitivity to such boundary conditions has been shown to explain discrepancies in theoretical predictions for cylinder diffusion by Broersma vs. those by de la Tone, particularly for rods with modest aspect ratios. Yet, the robustness of the overall lengths derived from either ellipsoidal or cylindrical geometries suggests that both the translational and rotational diffusion rates are dominated by this parameter. This is consistent with Equation (12), which suggests that H(AR) is nearly constant and does not vary dramatically between different models for elongated nanoparticles. In contrast, reasonable estimates of the aspect ratio apparently require that the model geometry closely matches the actual morphologies of the particles. This suggests that the approach for analyzing translational and rotational diffusion data introduced here has yet another advantage: instead of trying to determine values for AR that are highly sensitive to the specific model geometry, our approach first estimates the overall particle length L. This estimate can then be used to evaluate whether the underlying geometrical model can possibly yield reasonable AR values.

Example Methods

Figure 10:
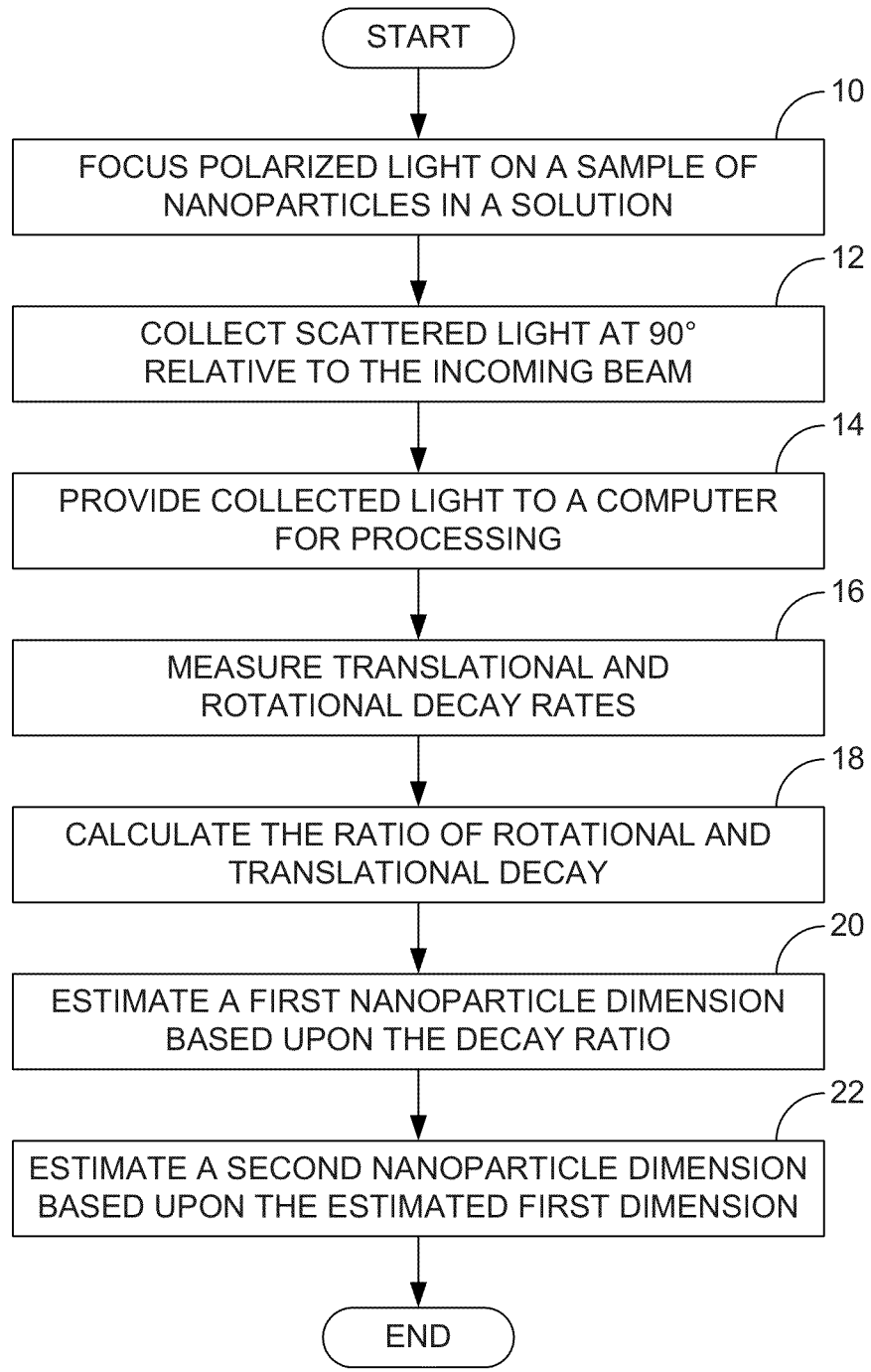
FIG. 10 is a flow diagram of an embodiment of a method for determining the dimensions of nanoparticles.

FIG. 10 is a flow diagram that provides an overview of an example method for determining nanoparticle dimensions consistent with the above discussion. As is apparent from that discussion, the dimensions of a nanoparticle can be determined in relation to how quickly the particles diffuse in translation and rotation within their solution as a result of Brownian motion. As can be expected, larger nanoparticles resist such diffusion to a greater extent than smaller nanoparticles.

As described above, the dimensions of suspended nanoparticles can be determined using a system such as that shown in FIG. 1. With such a system, polarized light is focused on a sample of nanoparticles suspended in a solution, as indicated in block 10 of FIG. 10. As was described above, the light can, for example, be laser light from a 35 mW single-mode HeNe laser at $\lambda=633$ nm that is passed through a Glan-Thompson prism (GT1) that increases the polarization purity to a nominal ratio of 100,000:1. The polarized beam can, for example, be focused on the sample using a focusing lens with f=100 mm, which results in a beam waist of approximately 80 μm diameter at the center of the sample. An aperture can be used to prevent stray light from entering the focusing lens.

When the polarized light reflects off of the nanoparticles as they diffuse within the solution, the light is scattered. The scattered light can then be collected at 90° relative to the incoming beam, indicated in block 12 of FIG. 10. A second Glan-Thompson prism can be used to select either vertically polarized (v-v) or horizontally depolarized (v-h) scattered light, and an adjustable iris diaphragm can be used to select the solid angle of scattered light imaged onto a photon detector, thereby determining the number of coherence areas that are contributing to the signal. In some embodiments, a focusing lens (f=81 mm) can be used to focus the scattered light onto the input of a multimode optical fiber (diameter=100 μm) coupled to a photon detector, such as an avalanche photodiode (APD) having a dark-count rate of 250 cps and a dead-time of 50 ns.

The scattered light data collected by the photon detector can then be provided to a computing device for processing, as indicated in block 14 of FIG. 10. In some embodiments, transistor-transistor logic (TTL) pulses from the APD (>2.5 V, 35 ns wide) can be fed into a commercial counter/timer board that is connected via a USB interface to a personal computer. An example of such data is shown in FIG. 3A.

Because of the interference between the light scattered by the diffusing nanoparticles, bright spots are detected by the photon detector. The average time for a bright spot to decay (i.e., to go from bright to dark) depends upon the size of the nanoparticles, and therefore can be used as an indication of nanoparticle size. FIG. 5 illustrates example measured translational and rotational decay rates, which can therefore be measured by the system, as indicated in block 16. As described above, the ratio of the rotational decay rate to the translational decay rate is highly sensitive to a dimension of the nanoparticle but highly insensitive to another dimension of the nanoparticles. In the case of nanorods having a cylindrical or ellipsoid geometry, the decay rate ratio is highly sensitive to the length of the nanoparticles and highly insensitive to the diameter or width of the nanoparticles.

Irrespective of the nanoparticle geometry, the decay rate ratio can be used to estimate a first dimension of the nanoparticle, thereby leaving only one other dimension to be calculated. That other dimension can then be estimated using the estimation of the first dimension. Accordingly, with reference back to FIG. 10, the decay rate ratio can be calculated (block 18), a first nanoparticle dimension (e.g., length) can be estimated based upon the decay rate ratio (block 20), and then a second nanoparticle dimension (e.g., AR or diameter) can be estimated based upon the first nanoparticle dimension. Equation 12 is an example equation that can be used to estimate the length of nanorods using the decay rate ratio $L_{rot}/\Gamma_{tr}$. In that equation, the function H(AR) is model-specific for nanorod geometries. However, the function can be modified for other nanoparticle geometries, if desired. Regardless of the nanoparticle geometry, however, the first dimension (length) is estimated using the ratio $\Gamma_{rot}/\Gamma_{tr}$. Equation 13 is an example equation that can be used to estimate the aspect ratio of nanoparticles using the estimated length. Again, this equation is specific to nanorod geometries but can be modified for other geometries, if desired.

The invention claimed is:

1. A method for determining the dimensions of nanoparticles, the method comprising:
    focusing light on a sample of nanoparticles suspended in a solution;
    collecting light scattered by the nanoparticles;
    measuring translational and rotational decay rates of the collected light;
    calculating a ratio of the rotational decay rate to translational decay rate; and
    estimating a first dimension of the nanoparticles based upon the decay rate ratio.

2. The method of claim 1, wherein measuring the translational and rotational decay rates of the nanoparticles comprises identifying bright spots in the collected light and measuring their rates of decay.

3. The method of claim 1, wherein calculating a ratio of the rotational decay rate to translational decay rate comprises dividing the rotational decay rate by the translational decay rate to obtain $\Gamma_{rot}/\Gamma_{tr}$.

4. The method of claim 3, wherein calculating a first dimension comprises calculating an average length of the nanoparticles based upon $\Gamma_{rot}/\Gamma_{tr}$.

5. The method of claim 4, wherein calculating an average length comprises calculating the average length using the following relation:

$$L = q^{-1}\sqrt[6]{54(\Gamma_{rot}/\Gamma_{tr})^{-1}H(AR)}$$

wherein L is the average length, q is a scattering vector of a system used to collect light scattered by the nanoparticles, and H(AR) is a function of an aspect ratio of the nanoparticles.

6. The method of claim 5, wherein the function H(AR) is dependent upon a modeled geometry of the nanoparticles.

7. The method of claim 1, further comprising estimating a second dimension of the nanoparticles based upon the estimated first dimension.

8. The method of claim 7, wherein the estimated first dimension is an average length of the nanoparticles and wherein the estimated second dimension is an average aspect ratio of the nanoparticles.

9. A system for determining dimensions of nanoparticles, the system comprising:
a computing device including a processing device and memory, the memory storing a nanoparticle dimension determination system that is configured to receive scattered light data collected by focusing light on a sample of nanoparticles suspended in a solution, measure translational and rotational decay rates of the scattered light data, calculate a ratio of the rotational decay rate to translational decay rate, and estimate a first dimension of the nanoparticles based upon the decay rate ratio.

10. The system of claim 9, wherein the nanoparticle dimension determination system is configured to measure the translational and rotational decay rates of the scattered light data by identifying bright spots in the collected light and measuring their rates of decay.

11. The system of claim 9, wherein the nanoparticle dimension determination system is configured to calculate the ratio of the rotational decay rate to translational decay rate by dividing the rotational decay rate by the translational decay rate to obtain $\Gamma_{rot}/\Gamma_{tr}$.

12. The system of claim 11, wherein the nanoparticle dimension determination system is configured to calculate the first dimension by calculating an average length of the nanoparticles based upon $\Gamma_{rot}/\Gamma_{tr}$.

13. The system of claim 12, wherein the nanoparticle dimension determination system is configured to calculate the average length by calculating the average length using the following relation:

$$L = q^{-1}\sqrt[6]{54(\Gamma_{rot}/\Gamma_{tr})^{-1}H(AR)}$$

wherein L is the average length, q is a scattering vector of the system, and H(AR) is a function of an aspect ratio of the nanoparticles.

14. The system of claim 13, wherein the function H(AR) is dependent upon a modeled geometry of the nanoparticles.

15. The system of claim 9, further comprising estimating a second dimension of the nanoparticles based upon the estimated first dimension.

16. The system of claim 15, wherein the estimated first dimension is an average length of the nanoparticles and wherein the estimated second dimension is an average aspect ratio of the nanoparticles.

17. The system of claim 9, further comprising:
a light source adapted to shine light on the nanoparticles;
a first polarization device adapted to increase a polarization purity of the light from the light source prior to it reaching the nanoparticles;
a sample chamber adapted to contain the nanoparticles and their solution;
a second polarization device adapted to select vertically-polarized or horizontally-polarized light scattered by the nanoparticles; and
a photon detector adapted to collect the scattered polarized light.

18. A non-transitory computer-readable medium that stores a nanoparticle dimension determination system comprising:
logic configured to receive scattered light data collected by focusing light on a sample of nanoparticles suspended in a solution;
logic configured to measure translational and rotational decay rates of the scattered light data;
logic configured to calculate a ratio of the rotational decay rate to translational decay rate; and
logic configured to estimate a first dimension of the nanoparticles based upon the decay rate ratio.

19. The computer-readable medium of claim 18, wherein the logic configured to estimate the first dimension is configured to calculate an average length of the nanoparticles using the relation:

$$L = q^{-1}\sqrt[6]{54(\Gamma_{rot}/\Gamma_{tr})^{-1}H(AR)}$$

wherein L is the average length, q is a scattering vector of the system, $\Gamma_{rot}/\Gamma_{tr}$ is the decay rate ratio, and H(AR) is a function of an aspect ratio of the nanoparticles.

20. The computer-readable medium of claim 19, further comprising logic configured to estimate a second dimension of the nanoparticles based upon the estimated first dimension.

* * * * *